(12) United States Patent
Govari et al.

(10) Patent No.: US 9,005,192 B2
(45) Date of Patent: Apr. 14, 2015

(54) SIMULTANEOUS ABLATION BY MULTIPLE ELECTRODES

(75) Inventors: Assaf Govari, Haifa (IL); Andres Claudio Altmann, Haifa (IL); Yaron Ephrath, Karkur (IL)

(73) Assignee: Biosense Webster (Israel) Ltd. (IL)

( * ) Notice: Subject to any disclaimer, the term of this patent is extended or adjusted under 35 U.S.C. 154(b) by 993 days.

(21) Appl. No.: 12/941,165

(22) Filed: Nov. 8, 2010

(65) Prior Publication Data

US 2012/0116386 A1    May 10, 2012

(51) Int. Cl.
| | |
|---|---|
| A61B 18/14 | (2006.01) |
| A61B 18/12 | (2006.01) |
| A61B 18/00 | (2006.01) |
| A61B 19/00 | (2006.01) |
| A61B 18/16 | (2006.01) |

(52) U.S. Cl.
CPC ......... *A61B 18/1206* (2013.01); *A61B 18/1492* (2013.01); *A61B 2018/00577* (2013.01); *A61B 2018/00875* (2013.01); *A61B 2018/1286* (2013.01); *A61B 2018/1467* (2013.01); *A61B 2019/5251* (2013.01); *A61B 2018/128* (2013.01); *A61B 18/16* (2013.01); *A61B 2018/00821* (2013.01)

(58) Field of Classification Search
USPC .............................................. 606/34, 37, 41
See application file for complete search history.

(56) References Cited

U.S. PATENT DOCUMENTS

| | | | |
|---|---|---|---|
| 5,542,916 A * | 8/1996 | Hirsch et al. ..................... 604/22 | |
| 5,782,828 A | 7/1998 | Chen et al. | |
| 5,931,835 A | 8/1999 | Mackey | |
| 5,954,686 A | 9/1999 | Garito | |
| 6,027,500 A | 2/2000 | Buckles et al. | |
| 6,254,600 B1 | 7/2001 | Willink | |
| 6,582,427 B1 * | 6/2003 | Goble et al. ..................... 606/37 |
| 6,730,078 B2 * | 5/2004 | Simpson et al. ................ 606/34 |
| 7,468,062 B2 | 12/2008 | Oral et al. | |
| 2002/0022836 A1 * | 2/2002 | Goble et al. ..................... 606/34 |
| 2003/0130711 A1 | 7/2003 | Pearson et al. | |
| 2003/0153908 A1 * | 8/2003 | Goble et al. ..................... 606/41 |
| 2003/0163123 A1 * | 8/2003 | Goble et al. ..................... 606/34 |
| 2003/0163124 A1 * | 8/2003 | Goble ............................. 606/37 |
| 2003/0199862 A1 * | 10/2003 | Simpson et al. ................ 606/34 |

(Continued)

FOREIGN PATENT DOCUMENTS

EP    1334699 A1    8/2003

OTHER PUBLICATIONS

EP Search Report Appln No. 11 18 8103 dated Feb. 24, 2012.

(Continued)

*Primary Examiner* — Joseph Stoklosa
*Assistant Examiner* — Jocelyn D Ram

(57) ABSTRACT

Apparatus, including a current source which has a transformer having a primary winding coupled to receive input power. The transformer has a secondary winding having a first plurality of secondary taps configured to supply electrical power at an ablation frequency to an electrode in contact with body tissue. The tissue has an impedance, and is ablated by the electrical power. The current source has a second plurality of capacitors. The apparatus also includes a controller which is configured to select one of the secondary taps and at least one of the capacitors in response to the impedance and the ablation frequency, and to connect the selected secondary tap to the selected at least one of the capacitors.

10 Claims, 5 Drawing Sheets

(56) References Cited

U.S. PATENT DOCUMENTS

| | | |
|---|---|---|
| 2005/0245922 A1* | 11/2005 | Goble .................... 606/37 |
| 2006/0030845 A1* | 2/2006 | Leung et al. ............ 606/41 |
| 2006/0155270 A1 | 7/2006 | Hancock |
| 2007/0129716 A1 | 6/2007 | Daw |
| 2007/0191827 A1 | 8/2007 | Lischinsky |
| 2007/0225699 A1* | 9/2007 | Goble et al. ............ 606/34 |
| 2008/0058635 A1 | 3/2008 | Halperin et al. |
| 2008/0294156 A1* | 11/2008 | Newton et al. ......... 606/34 |
| 2009/0062786 A1* | 3/2009 | Garito et al. ........... 606/37 |
| 2010/0145329 A1 | 6/2010 | Bystryak |
| 2012/0116387 A1* | 5/2012 | Govari et al. .......... 606/41 |

OTHER PUBLICATIONS

EP Search Report Appln No. 11 18 8096 dated Feb. 28, 2012.

European Search Report, for EPA Appln. No. 13159798.1-1652, dated Jun. 11, 2013.

* cited by examiner

SIMULTANEOUS ABLATION BY MULTIPLE ELECTRODES

FIELD OF THE INVENTION

The present invention relates generally to invasive medical devices, and specifically to ablation of tissue using such devices.

BACKGROUND OF THE INVENTION

Ablation of body tissue, using multiple electrodes, is known in the art. The ablation is typically performed by applying alternating currents to the electrodes, at a sufficient power to cause the ablation. Typically, the electrodes are mounted on a distal tip of a catheter which is inserted into a lumen of a subject.

The distal tip may be tracked in a number of different ways known in the art, for example by measuring magnetic fields, generated by coils external to the subject, at the distal tip.

U.S. Pat. No. 5,931,835 to Mackey, whose disclosure is incorporated herein by reference, describes a radio frequency energy delivery system for multipolar electrode catheters. The disclosure states that the electrodes may be simultaneously energized in phase with each other to achieve a desired lesion pattern.

U.S. Pat. No. 5,782,828 to Chen, et al., whose disclosure is incorporated herein by reference, describes an ablation catheter having multiple electrodes and a close-loop control mechanism for each electrode with a temperature sensor.

U.S. Pat. No. 7,468,062 to Oral, et al., whose disclosure is incorporated herein by reference, describes an atrial ablation catheter with an electrode array.

U.S. Pat. No. 6,027,500 to Buckles, et al., whose disclosure is incorporated herein by reference, describes a catheter with a plurality of electrodes disposed adjacent to a distal end of the catheter. One of the electrodes is an ablation electrode.

U.S. Patent Application 2008/0058635 to Halperin, et al., whose disclosure is incorporated herein by reference, describes a magnetic resonance imaging system including an invasive combined electrophysiology and imaging antenna catheter having diagnostic electrodes for receiving electrical potentials.

The description above is presented as a general overview of related art in this field and should not be construed as an admission that any of the information it contains constitutes prior art against the present patent application.

SUMMARY OF THE INVENTION

An embodiment of the present invention provides apparatus, including:

a current source, including:

a transformer having a primary winding coupled to receive input power and a secondary winding having a first plurality of secondary taps configured to supply electrical power at an ablation frequency to an electrode in contact with body tissue so as to ablate the tissue, the tissue having an impedance; and a second plurality of capacitors; and a controller, configured to select one of the secondary taps and at least one of the capacitors in response to the impedance and the ablation frequency, and to connect the selected secondary tap to the selected at least one of the capacitors.

The controller may be configured to select only one of the capacitors for each respective secondary tap selected.

In a disclosed embodiment the selected secondary tap and at least one capacitor are connected in parallel so as to form a circuit resonating at the ablation frequency. The controller may be configured to measure a position of a section of a catheter including the electrode using positioning currents generated at the section, and wherein the ablation frequency is at least four times a frequency of the positioning currents.

The controller may be configured to measure the position of the section while ablating the tissue. Typically, the positioning currents include currents from the section into the tissue. The positioning currents may be generated in response to an alternating magnetic field in proximity to the section. In a further disclosed embodiment the selected secondary tap and at least one capacitor are connected in parallel so as to form a circuit filtering out the frequency of the positioning currents.

In an alternative embodiment the secondary tap is selected so that a desired level of the electrical power is a maximum power based on the input power.

In a further alternative embodiment the controller is configured to measure the impedance prior to ablating the tissue. Alternatively or additionally, the controller is configured to measure the impedance while ablating the tissue.

There is further provided, according to an embodiment of the present invention, a method, including:

coupling a primary winding of a transformer to receive input power;

configuring a first plurality of secondary taps of a secondary winding of the transformer to supply electrical power at an ablation frequency to an electrode in contact with body tissue so as to ablate the tissue, the tissue having an impedance;

providing a second plurality of capacitors;

selecting one of the secondary taps and at least one of the capacitors in response to the impedance and the ablation frequency; and connecting the selected secondary tap to the selected at least one of the capacitors.

There is further provided, according to an embodiment of the present invention, apparatus, including:

a first plurality of current sources operative at respective different frequencies, each current source including:

a respective transformer having a primary winding coupled to receive input power and a secondary winding having a second plurality of secondary taps configured to supply respective electrical power to a respective electrode in contact with body tissue, the tissue having a respective impedance; and a third plurality of capacitors; and a controller, configured to select, for each current source, one of the secondary taps thereof and at least one of the capacitors thereof in response to the respective impedance thereof and the respective frequency of the current source, and, for each current source, to connect the selected secondary tap thereof to the selected at least one of the capacitors thereof.

In one embodiment a sum of desired levels of the respective electrical power is equal to a preset overall power to be dissipated in the tissue.

There is further provided, according to an embodiment of the present invention, apparatus, including:

an energy generator, configured to supply first ablation power at a first frequency and second ablation power at a second frequency different from the first frequency; and a probe, including at least one electrode coupled to receive the first and second ablation powers simultaneously and to dissipate the first and second ablation powers in body tissue in contact with the at least one electrode.

The at least one electrode may be a single electrode. The single electrode may be configured as one of a first source electrode and a first return electrode for the first ablation power, and as one of a second source electrode and a second return electrode for the second ablation power.

In a disclosed embodiment the at least one electrode includes a first electrode coupled to receive the first ablation power and a second electrode coupled to receive the second ablation power. The first electrode may be configured as a source electrode for the first ablation power and as a return electrode for the second ablation power, and the second electrode may be configured as a source electrode for the second ablation power.

There is further provided, according to an embodiment of the present invention, a method, including:

operating a first plurality of current sources at respective different frequencies, each current source including:

a respective transformer having a primary winding coupled to receive input power and a secondary winding having a second plurality of secondary taps configured to supply respective electrical power to a respective electrode in contact with body tissue, the tissue having a respective impedance; and a third plurality of capacitors; and selecting, for each current source, one of the secondary taps thereof and at least one of the capacitors thereof in response to the respective impedance thereof and the respective frequency of the current source, and, for each current source, connecting the selected secondary tap thereof to the selected at least one of the capacitors thereof.

There is further provided, according to an embodiment of the present invention, a method, including:

supplying first ablation power at a first frequency and second ablation power at a second frequency different from the first frequency;

receiving with at least one electrode the first and second ablation powers simultaneously; and dissipating the first and second ablation powers in body tissue in contact with the at least one electrode.

The present invention will be more fully understood from the following detailed description of the embodiments thereof, taken together with the drawings in which:

DETAILED DESCRIPTION OF EMBODIMENTS

Overview

Figure 1:
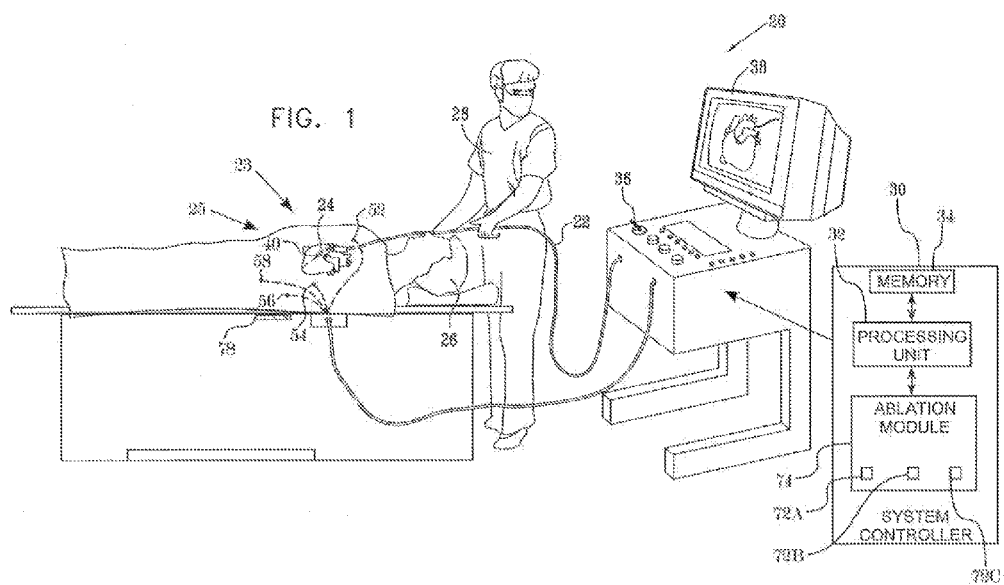
FIG. 1 is a schematic, pictorial illustration of a catheter ablating system, according to an embodiment of the present invention.

An embodiment of the present invention provides an improved system for ablating tissue with an ablating electrode attached to a probe, typically the distal tip of a catheter, while simultaneously tracking the position of the probe in a subject. In addition, the power dissipated while ablating the tissue may be maintained at a substantially fixed preset constant level, even if the impedance of the tissue changes.

In order to maintain the ablation power dissipated constant, power to the electrode is supplied from a current source that typically comprises a transformer with selectable secondary taps. A controller measures the power, and selects one of the taps so as to keep the power constant. Typically, the tap required depends on the impedance of the tissue being ablated.

In addition to supplying the power via selectable taps, the power is also filtered. The filtering is typically provided by choosing one or more capacitors, and connecting the chosen capacitors so as to provide a selectable capacitance across the selected tap in a parallel resonant circuit. The capacitance is selected so that the circuit resonates at the frequency used for ablating the tissue. Since the circuit is a parallel circuit it has a high impedance at the ablating frequency, and so has little effect on the power delivered to the ablating electrode and to the tissue.

The position of the probe in the subject may be tracked by measuring currents, termed positioning currents, generated between various electrodes, typically attached to the skin of the subject, and another electrode in the distal tip of the probe. The currents are alternating currents, typically at a frequency substantially different from the ablating frequency.

Alternatively or additionally, the position of the probe may be tracked by a magnetic tracking system. Such a system uses alternating magnetic fields to induce positioning currents in one or more coils in the distal tip, and the frequency of the induced currents is also typically substantially different from the ablating frequency.

Harmonics, including sub-harmonics, of the ablating frequency may correspond to the frequency of the positioning currents, and without filtration may cause errors in the measured probe position. However, because the ablation and positioning frequencies are different, the parallel circuit effectively short-circuits, i.e., filters out, the harmonics or sub-harmonics of the ablation frequency, so negating any errors they may cause.

Some embodiments of the present invention comprise more than one current source, each source being configured to simultaneously supply ablation power at a different frequency. Each current source may have a transformer with selectable secondary taps, and a selectable capacitance that can be connected across a selected tap, as described above. Alternatively, each current source may have a transformer with only one secondary (i.e., no taps in the secondary) and one capacitance, the secondary inductance and the capacitance being chosen to resonate at the frequency of the current source. Supplying the ablation power at different frequencies allows a controller in the system to measure and control the power dissipated by each current source individually and simultaneously.

DETAILED DESCRIPTION

Figure 2:
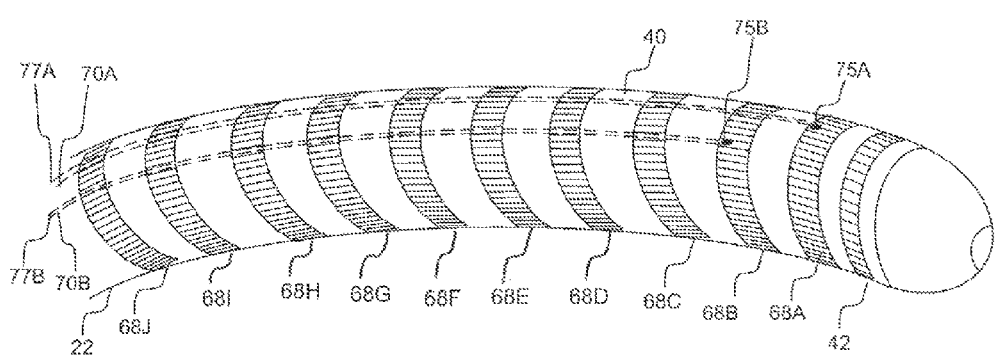
FIG. 2 is a schematic diagram of a distal tip of a catheter used in the system of FIG. 1, according to an embodiment of the present invention.

Reference is now made to FIG. 1, which is a schematic, pictorial illustration of a catheter ablating system 20, and to FIG. 2 which is a schematic diagram of a distal tip of a catheter 22 used in the system, according to embodiments of the present invention. In system 20, catheter 22 is inserted into a lumen 23, such as a chamber of a heart 24, of a subject 26. Typically, the catheter is used by a medical practitioner 28 during a procedure which includes performing ablation of tissue 25. However, the catheter may be configured to perform functions in addition to ablation, such as measuring potentials of heart tissue.

The functioning of system 20 is managed by a system controller (SC) 30, comprising a processing unit 32 communicating with a memory 34, wherein is stored software for operation of system 20. Controller 30 is typically an industry-standard personal computer (PC) comprising a general-purpose computer processor. However, in some embodiments, at least some of the functions of the controller are performed using custom-designed hardware and software, such as an application specific integrated circuit (ASIC) or a field programmable gate array (FPGA). Controller 30 is typically operated by practitioner 28 using a pointing device 36 and graphic user interface (GUI) 38, which enable the practitioner to set parameters of system 20. GUI 38 typically also displays results of the procedure to the medical practitioner.

The software in memory 34 may be downloaded to the controller in electronic form, over a network, for example. Alternatively or additionally, the software may be provided on non-transitory tangible media, such as optical, magnetic, or electronic storage media.

A distal tip 40 of catheter 22 comprises at least one electrode 42 which, in a disclosed embodiment, is used in tracking the position of the distal tip, as described below. However, electrode 42 may be used for other purposes, as well, such as for electrophysiological sensing. The electrode is connected by a wire (not shown) in catheter 22 to driver and measurement circuitry in system controller 30.

A plurality of body-surface electrodes, such as adhesive skin patches 52, 54, 56, and 58 (collectively referred to hereinbelow as patches 52-58) are coupled to a body-surface (e.g., the skin) of subject 26. Patches 52-58 may be placed at any convenient locations on the body-surface in the vicinity of the medical procedure. Typically, the locations of the skin patches are spaced apart. For example, for cardiac applications, patches 52-58 are typically placed around the chest of subject 26.

Patches 52-58 are also connected by wires to system controller 30. The system controller determines position coordinates of the distal tip inside heart 24 based on currents, herein termed positioning currents, measured between the at least one electrode 42 and each of patches 52-58. The currents, generated by current drivers in the system controller, are alternating currents having one or more frequencies in the region of 100 kHz. The frequencies of the alternating currents are herein termed current positioning frequencies, $f_{current\_posit}$. Using the determined position coordinates, the system controller is able to show the position of the distal tip inside the heart on GUI 38.

Alternatively or additionally, the distal tip may be tracked by other systems known in the art, for example, by a magnetic tracking system. One such magnetic tracking system is the CARTO 3 system, produced by Biosense Webster, Inc, Diamond Bar, Calif., which tracks the distal tip by using alternating magnetic fields to induce corresponding positioning currents in coils in the tip. The fields are typically set to alternate at frequencies of 1-3 kHz, but may be set to alternate at higher frequencies, up to 50 kHz or more. The frequencies of the magnetic fields are herein termed magnetic positioning frequencies, $f_{magnetic\_posit}$.

Distal tip 40 also comprises a multiplicity of ablation electrodes that are typically located on the outer surface of the distal tip. By way of example, tip 40 is herein assumed to comprise 10 electrodes 68A, 68B, 68C, 68D, 68E, 68F, 68G, 68H, 68I and 68J, but it will be understood that embodiments of the present invention may use any convenient plurality of ablation electrodes. The multiplicity of ablation electrodes (68A, 68B, 68C, 68D, 68E, 68F, 68G, 68H, 68I, 68J) are also herein individually or collectively termed ablation electrode(s) 68. Each electrode 68A, 68B, 68C, 68D, 68E, 68F, 68G, 68H, 68I, 68J is separately connected by a respective conducting wire 70A, 70B, 70C, 70D, 70E, 70F, 70G, 70H, 70I, 70J to a respective ablation current source 72A, 72B, 72C, 72D, 72E, 72F, 72G, 72H, 72I, 72J. Current sources 72A, 72B, 72C, 72D, 72E, 72F, 72G, 72H, 72I, 72J are located in an ablation module 74 in controller 30, and are under overall management of the controller.

Typically, ablation electrodes 68A, 68B, 68C, 68D, 68E, 68F, 68G, 68H, 68I, 68J have respective thermocouples 75A, 75B, 75C, 75D, 75E, 75F, 75G, 75H, 75I, 75J mounted on the electrodes. In one embodiment, wires 70A, 70B, 70C, 70D, 70E, 70F, 70G, 70H, 70I, 70J are of copper, and thermocouples 75A, 75B, 75C, 75D, 75E, 75F, 75G, 75H, 75I, 75J are implemented by connecting respective constantan (Cu/Ni) wires 77A, 77B, 77C, 77D, 77E, 77F, 77G, 77H, 77I, 77J . . . to wires 70A, 70B, 70C 70D, 70E, 70F, 70G, 70H, 70I, 70J at the ablation electrodes.

As is described in more detail below, current sources 72A, 72B, 72C, 72D, 72E, 72F, 72G, 72H, 72I, 72J supply their respective currents independently of each other. In addition, each current source is able to independently provide ablation current in a unipolar or a bipolar mode.

In the unipolar mode, the ablation current transfers from an ablation electrode 68, acting as a source electrode, to the tissue being ablated and the current path is completed via a return electrode 78, external to lumen 23. Return electrode 78 is typically placed in contact with the skin, for example the back, of subject 26, and acts as a local ground electrode.

In the bipolar mode, the ablation current transfers between pairs of ablation electrodes 68 via the tissue being ablated. In some embodiments each electrode 68 may be configured as either a source electrode or as a return electrode. For example, the ten electrodes may be arranged as five pairs 68A-68B, 68C-68D, 68E-68F, 68G-68H, 68I-68J. Typically, in this case all return electrodes are connected together.

Alternatively, each electrode 68 may be configured as a source electrode and as a return electrode. For example, the ten electrodes 68 of the exemplary embodiment described above may be arranged in nine pairs 68A-68B, 68B-68C, 68C-68D, 68D-68E, 68E-68F, 68F-68G, 68G-68H, 68H-68I, 68I-68J, wherein the eight electrodes 68B, 68C, 68D, 68E, 68F, 68G, 68H, 68I act as both source and return electrodes.

Figure 3:
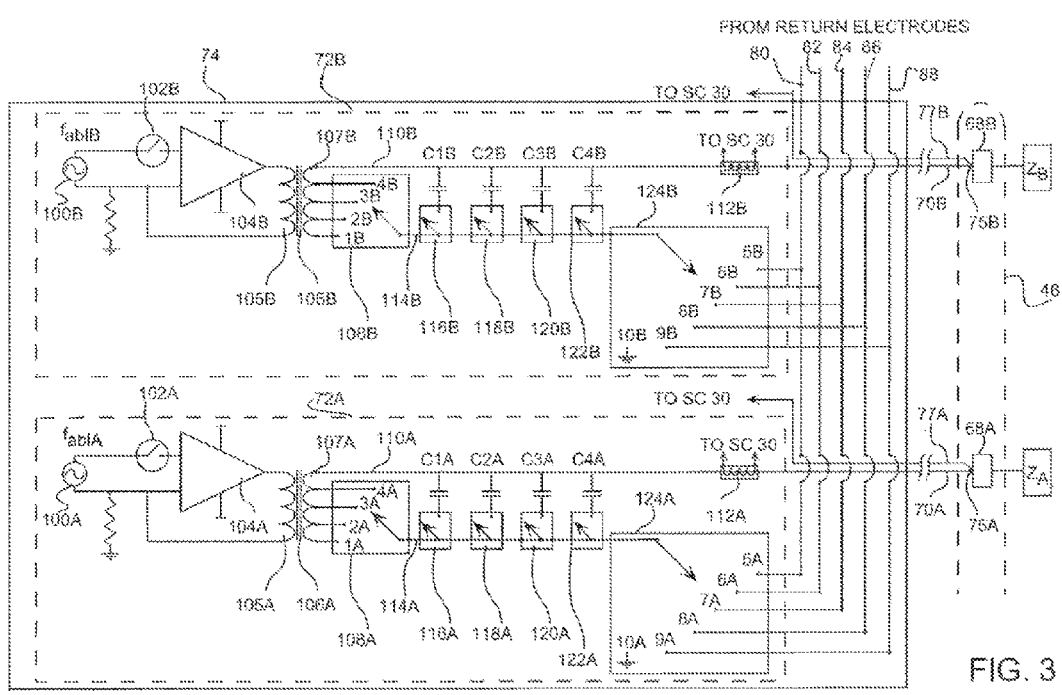
FIG. 3 is a schematic circuit diagram of current sources in an ablation module, according to an embodiment of the present invention.

FIG. 3 is a schematic circuit diagram of current sources 72A and 72B in module 74, according to an embodiment of the present invention. FIG. 3 also schematically illustrates some of the elements of distal tip 40, using the same identifying numerals as are used in the description of the elements above. As described in more detail below, ablation module 74 acts as a generator of ablation energy, and is also referred to herein as energy generator 74. Generator 74 comprises a respective current source for each electrode, but for simplicity only circuit diagrams for two current sources 72A, 72B, are shown in FIG. 3. Thus, for the exemplary embodiment described above, there are ten current sources. In one embodiment, generator 74 is constructed as two separate printed circuit boards each having five current sources and five return lines; the return lines are described in more detail below.

Each current source 72A, 72B, . . . is constructed from substantially similar components, and all sources perform substantially the same function of supplying ablation power, in the form of ablating current, to a respective electrode. All adjustable elements of generator 74, such as the switches and amplifiers of the current sources, are under overall control of controller 30.

Except where otherwise indicated, the following description applies to current source 72A, wherein elements of the source have a suffix A after the identifying numeral. Substantially the same description applies to other current sources in generator 74, such as current source 72B, and those having ordinary skill in the art will be able to adapt the description for the other current sources, mutatis mutandis, for example by altering the suffix of the identifying numeral.

Current source 72A comprises a frequency generator 100A, typically a phase-locked loop device, which supplies a driving alternating voltage to the current source. The frequency of the alternating voltage provided by generator 100A, herein termed the ablation frequency $f_{ablA}$, is set by controller 30, and is typically in the range of 400-600 kHz, although other frequencies may be used. The ablation frequency is typically at least four times the positioning frequency $f_{current\_posit}$ or $f_{magnetic\_posit}$.

The other current sources in generator 74 comprise respective frequency generators 100B, 100C, ..., generating respective ablation frequencies $f_{ablB}$, $f_{ablC}$, .... Each frequency $f_{ablB}$, $f_{ablC}$, ..., while typically being in an overall band of approximately 50 kHz, is different. For simplicity, in the following description, the different frequencies may be collectively referred to as $f_{abl}$.

Current source 72A comprises an on-off switch 102A, coupled to a power amplifier 104A, typically at the input of the amplifier. Switch 102A allows unit 32 to toggle the amplifier between an "on" state wherein the amplifier outputs ablating power to other elements of the current source, and an "off" state wherein no power is supplied to the other elements.

In its "on" state power amplifier 104A typically outputs power, at a steady state, up to approximately 100 W. The maximum power in a steady state is represented herein as $P_{MAX}$. Controller 30 typically operates amplifier 104A at $P_{MAX}$ during ablation, but may operate the amplifier at values lower than $P_{MAX}$, including at values at which ablation does not occur. In an embodiment, amplifier 104A comprises a Model PA119 device, produced by Cirrus Logic, Inc. of Austin, Tex. The PA119 is stated to supply, when operating in a steady state, a power of up to 70 W, i.e., $P_{MAX}$=70 W.

The output of amplifier 104A is connected across the primary winding 105A of a transformer 106A. The secondary winding 107A of the transformer comprises a plurality of taps, each tap corresponding to a respective secondary inductance of the transformer. A particular tap is selected by a multi-pole tap selection switch 108A. By way of example, in an embodiment illustrated in FIG. 3, the secondary of transformer 106A is herein assumed to have four taps 1A, 2A, 3A, 4A, having respective step-down ratios of 3:1, 3.5:1, 4:1, and 5:1. However, other embodiments may have other numbers of taps, with other ratios.

The secondary of transformer 106A has a first output rail 110A which acts as a common rail for all the secondary taps. Rail 110A is connected via conducting wire 70A to ablation electrode 68A. The other current sources in generator 74 have common rails similar to rail 110A, each common rail connecting to a respective ablation electrode. Thus, as shown in FIG. 3, source 72B has a common rail 110B, connected via conducting wire 70B, to ablation electrode 68B.

Typically, a sensing element 112A is placed in series with rail 110A, to enable controller 30 to determine a power input to electrode 68A and an impedance presented by the electrode. Element 112A typically comprises a current sensing transformer, which enables the controller to measure the current in rail 110A. A suitable current sensing transformer is a CST device produced by Coilcraft, of Cary Ill. Alternatively, other methods for determining the power input to the electrode as well as its impedance, such as by the controller measuring voltages across the windings or the taps of transformer 106A, may be used.

A second output rail 114A of the secondary of transformer 106A connects via tap selection switch 108A to one of the taps of the transformer. A plurality of capacitors C1A, C2A, C3A, C4A are connected, via respective capacitor-switches 116A, 118A, 120A, 122A, between common rail 110A and rail 114A. The number of capacitors is typically equal to the number of secondary taps on transformer 106A. In one embodiment the values of capacitors C1A, C2A, C3A, and C4A are respectively 3 nF, 5 nF, 8 nF, and 19 nF. Alternatively, the number of capacitors may be less than the number of secondary taps, and a desired capacitance may be achieved by using two or more capacitors.

Capacitors C1A, C2A, C3A, C4A are in parallel with the secondary of transformer 106A, so that any one of the capacitors, or a combination of them, can form a parallel LC (inductance-capacitance) circuit with any one of the taps of the transformer.

Second output rail 114A is connected, via a multi-pole mode selection switch 124A, to an ablation power return electrode. For unipolar mode operation, switch 124A is switched to pole 10A, which is connected to return electrode 78 (FIG. 1). For bipolar mode operation, switch 124 is switched to any of the other poles 5A-9A. Each pole 5A-9A is connected to a respective return wire 80, 82, 84, 86, and switches (not shown in the figure) couple the return wires to a different return electrode 68. For example, for bipolar operation with electrode 68A acting as a source electrode for current source 72A ablation power, and electrode 68B acting only as a return electrode for the ablation power, return wire 80 may be connected to electrode 68B and switch 102B may be switched off.

If electrode 68B is to act also as a source electrode, for current source 72B ablation power, then switch 102B is switched on. In this case further circuitry, which will be apparent to those having ordinary skill in the art, is coupled to electrode 68B allowing it to act as a return electrode at $f_{ablA}$, and as a source electrode for $f_{ablB}$. The circuitry typically comprises applying to electrode 68B power having the same frequency ($f_{ablA}$) and amplitude, but opposite phase, as the power applied to electrode 68A. In general, it will be appreciated that alternatively such circuitry may be configured to allow one single electrode 68 to act as a source electrode for two frequencies, or to act as a return electrode for the two frequencies.

For simplicity, such circuitry is not shown in FIG. 3, and except as otherwise indicated below, the following description assumes that an electrode 68 acts as either a source electrode or as a return electrode.

The ablation current generated by source 72A flows via electrode 68A through an impedance $Z_A$, herein also termed the tissue-impedance, of subject 26. If the source is operating in unipolar mode, the tissue-impedance occurs between electrode 68A and return electrode 78. If the source is operating in bipolar mode, the impedance is between electrode 68A and the selected return electrode. Tissue-impedance $Z_A$ typically varies, depending on parameters such as the position of the distal tip in subject 26, whether the tip is in contact with a lumen wall of the subject, and if it is in contact, an area of the contact.

(The ablation currents of the other current sources in generator 74 flow through different respective electrodes, and each current source has its own respective tissue-impedance. Thus, the ablation current from current source 72B flows via electrode 68B through a tissue-impedance $Z_B$.)

Thermocouple 75A is mounted on electrode 68A. Constantan wire 77A of the thermocouple is connected to system controller 30, which measures the voltage developed by the thermocouple and thus the temperature of electrode 68A.

As stated above, controller 30 may select one of a number of secondary taps on transformer 106A, and the same is true for the other transformers in generator 74. The external power dissipated by a given current source in its respective tissue-impedance is typically substantially dependent on the selected secondary tap of the respective transformer, as is explained with reference to FIG. 4.

Figure 4:
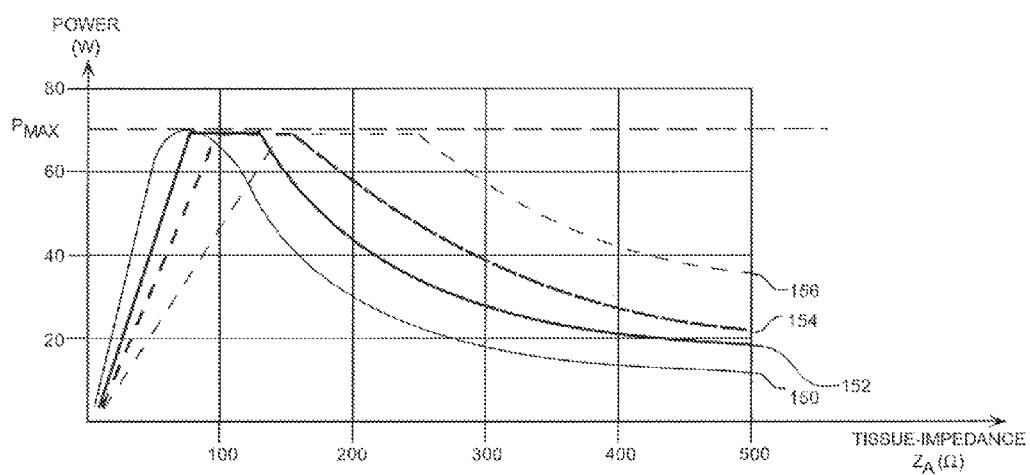
FIG. 4 shows schematic graphs illustrating power dissipated by a current source in a tissue-impedance vs. the value of the impedance, according to an embodiment of the present invention.

FIG. 4 shows schematic graphs illustrating power dissipated by source 72A in tissue-impedance $Z_A$ vs. the value of the impedance, according to an embodiment of the present invention. Graphs 150, 152, 154, 156 respectively illustrate the power dissipated in the tissue-impedance according to the tap 1A, 2A, 3A, 4A, of switch 108A that is selected. Substantially similar graphs apply for the other current sources of generator 74, and those having ordinary skill in the art will be able to adapt the following description, mutatis mutandis, for the other sources.

The graphs are assumed to be plotted for a situation wherein power amplifier 104A outputs a maximum power $P_{MAX}$ equal to 70 W. For each graph, the power dissipated in the tissue peaks when the impedance of the tapped secondary circuit approximately equals the tissue-impedance $Z_A$.

As described below with reference to FIG. 5, controller 30 selects the tap according to the measured impedance of the tissue.

In one embodiment, illustrated in FIG. 4, tissue-impedance $Z_A$ is assumed to vary between approximately 50Ω and approximately 250Ω, and taps 1A, 2A, 3A, 4A are configured so that the peaks of the graphs cover the overall range of 50Ω-250Ω.

Returning to FIG. 3, consideration of the circuit of source 72A shows that the secondary taps and the capacitors may form a number of different parallel LC circuits. In embodiments of the present invention, the values of capacitors C1A, C2A, C3A, and/or C4A are chosen so that for each tap, a parallel LC circuit may be configured, using switches 108A, 116A, 118A, 120A, that is resonant at the ablation frequency $f_{ablA}$. Similarly, for the other current sources, a parallel LC circuit may be configured, by appropriate choice of the tap and capacitors of the circuit, that is resonant at the respective ablation frequency $f_{abl}$ of the source.

During ablation, the output of power amplifier 104A is typically predominantly at the ablation frequency. However, the amplifier also produces harmonics and subharmonics of the ablation frequency, and one or more of these may correspond with one or more of the positioning frequencies. When this occurs, it causes errors in the measured position of the distal tip.

Embodiments of the present invention overcome the problem caused by the production of harmonics and subharmonics by configuring, for a given secondary tap, that the tap is part of a parallel LC circuit that is resonant at the ablation frequency $f_{abl}$ of the respective source. The configuration is by selection of one or more capacitors to be in parallel with the tap. The parallel circuit formed acts as a high impedance at this frequency, and consequently causes little or no reduction in ablation power delivered to the tissue being ablated. However, because of the difference in frequencies between the ablation frequency, $f_{abl}$, and the positioning frequencies, the parallel circuit acts as a low impedance at the positioning frequencies. Consequently, the parallel circuit effectively short-circuits and filters out the positioning frequencies, so negating any errors that are otherwise caused by the harmonics or subharmonics of the ablation frequency corresponding with a positioning frequency.

In addition, the multiplicity of available taps allow the tap that is chosen for the parallel LC circuit to be optimal with respect to the tissue impedance. In other words, the tap for the LC circuit may be selected to approximately match the tissue impedance, so that maximum power is delivered to the tissue. Thus, as described below with respect to the flowchart of FIG. 5, the same secondary tap is used to filter out the positioning frequencies and to match the tissue impedance.

Figure 5:
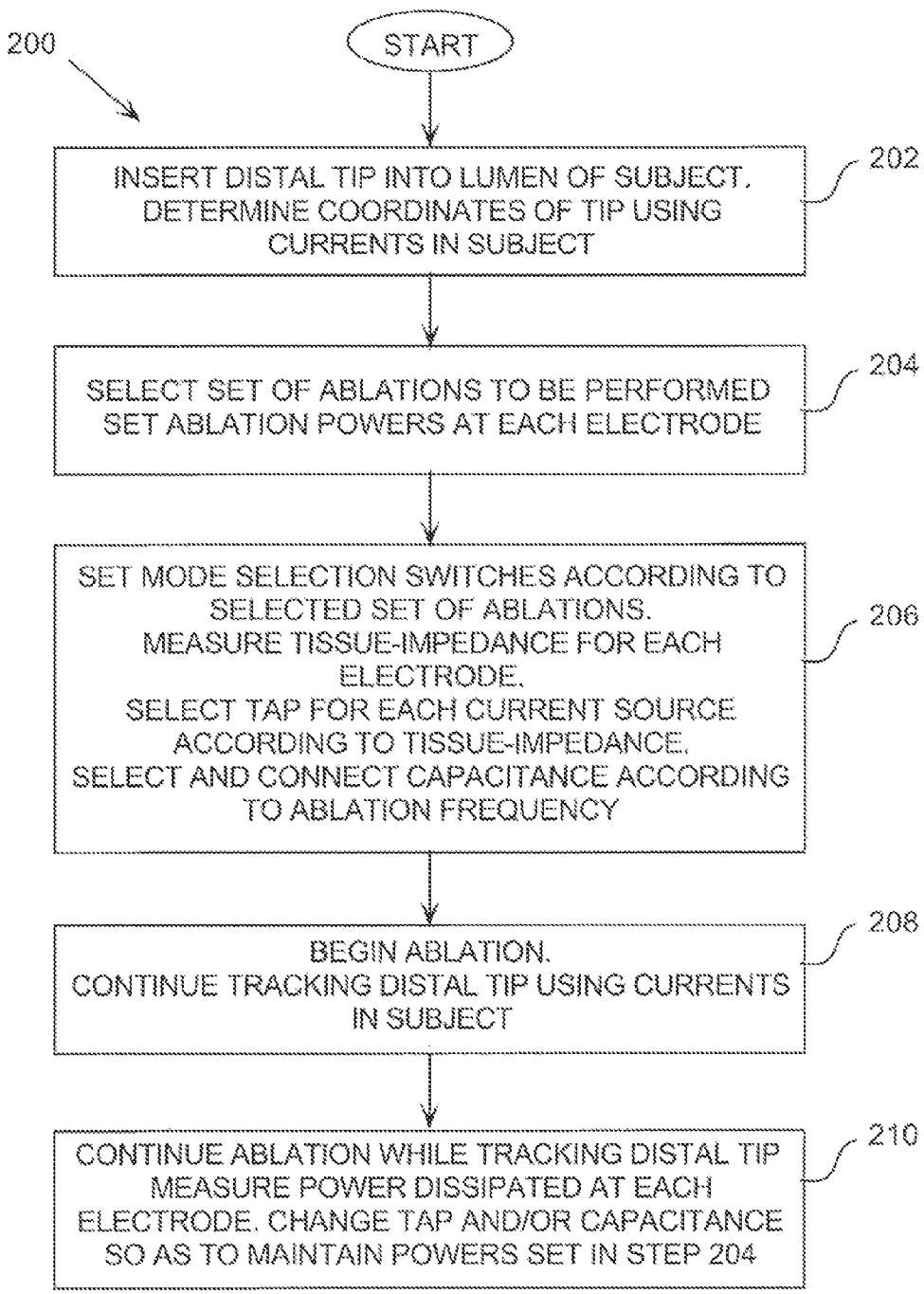
FIG. 5 is a flowchart of an ablation procedure performed by a practitioner, according to an embodiment of the present invention.

FIG. 5 is a flowchart 200 of an ablation procedure performed by practitioner 28, according to an embodiment of the present invention. In an initial step 202, the practitioner introduces the distal tip of catheter 22 into lumen 23, herein assumed by way of example to comprise the left atrium of heart 24. As explained above with reference to FIG. 1, system controller 30 determines position coordinates of the distal tip based on currents measured to patches 52-58, and presents the position of the distal tip to the practitioner using GUI 38.

In a first procedure setup step 204, the practitioner selects a set of ablations to be performed in the procedure. The selection typically comprises choosing which ablation electrodes 68 are to be used in the procedure, and the power to be dissipated by each electrode. In addition, an overall maximum total power, for example 400 W, that is to be dissipated in the tissue by all the ablation electrodes during the procedure may be set. In the following description, by way of example it is assumed that the power to be dissipated by each electrode is set to $P_{max}$. The practitioner may also set, for each electrode, whether the ablation is to be unipolar or bipolar. In the case of bipolar ablation, the practitioner selects the return electrode to be used.

In a second procedure setup step 206, the system controller sets each mode selection switch 124A, 124B according to the selection made in step 204. The controller then measures a tissue-impedance for each electrode that is to be used in the procedure. The measurement may be made by the controller operating each power amplifier 104A, 104B under known non-ablative conditions, and measuring the current into the respective ablation electrodes, and the voltage across the electrodes, using sensing elements 112A, 112B.

From the measured impedance for each electrode the controller uses tap selection switches 108A, 108B to select the tap for each respective current source necessary for each electrode to dissipate $P_{max}$, as described above with reference to FIG. 4.

For each respective current source the controller also connects one or more capacitors in parallel with the selected tap, using the capacitor-switches. For example, for current source 72B the controller activates one or more of switches 116B, 118B, 120B, 122B. The capacitors are selected so that, together with the tap, they form a parallel resonant circuit resonating at the ablation frequency.

In a start ablation step 208, the practitioner begins ablating tissue in the lumen, by having the controller operate power amplifiers 104A, 104B at ablative conditions. While ablation is being performed, the controller continues to track the position coordinates of the distal tip based on currents measured to patches 52-58, and the position of the distal tip continues to be presented on GUI 38.

In a continuing ablation step 210, while the practitioner is performing the ablation, the controller measures the power dissipated at each electrode using sensing elements 112A, 112B. As necessary, for each electrode the processor changes the tap on the corresponding transformer, and the capacitance across the tap, so as to maintain the power dissipation conditions set in step 204. The ablation at each electrode typically continues until stopped by the practitioner. Alternatively or additionally, the processor stops the ablation at a particular electrode when a preset temperature, measured by the thermocouple 75A, 75B in contact with the electrode, is reached.

Consideration of the description above illustrates that the elements of the parallel circuits for each current source are selected independently to satisfy multiple conditions. The tap of a given circuit is selected according to the power dissipated in the tissue-impedance presented to the current source's ablation electrode. The capacitance is selected so that the inductance of the tap, taken together with the capacitance, acts substantially as an open-circuit at the ablation frequency, and as a short-circuit at the positioning frequencies. The same tap is thus used for impedance matching to the tissue and filtering of the ablation and positioning frequencies.

The embodiments described above with reference to FIG. 3 have assumed that each current source comprises a transformer with selectable secondary taps, giving different inductances. Each current source also has a selectable capacitance in parallel with the secondary tap. Some embodiments of the present invention typically have, for each current source, one preselected inductance in parallel with one preselected capacitance, the value of the inductance and the capacitance being chosen to resonate with the ablation frequency generated by the particular current source. In order to alter the power dissipated by the electrode coupled to receive the ablation frequency, a method different from that described above, and which will be familiar to those having ordinary skill in the art, such as altering the gain of the power amplifier of the current source, may be used.

The embodiments described above exemplify the principle that supplying the ablation power to one or more electrodes at different frequencies enables measurement and control of the power dissipated, by each current source of an ablation system, in body tissue in contact with the one or more electrodes. The measurement and control may be performed individually and simultaneously for each source.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
an energy generator, configured to supply first ablation power at a first frequency and second ablation power at a second frequency different from the first frequency, the generator further including a transformer with at least two selectable secondary taps and a controller, the controller configured to measure the first and the second ablation power and select one or more of the taps to keep the first and the second ablation powers, respectfully, constant; and
a probe, comprising at least one electrode coupled to receive the first and second ablation powers simultaneously and to dissipate the first and second ablation powers in body tissue in contact with the at least one electrode.

2. The apparatus according to claim 1, wherein the at least one electrode comprise consists of a single electrode.

3. The apparatus according to claim 2, wherein the single electrode is configured as one of a first source electrode and a first return electrode for the first ablation power, and as one of a second source electrode and a second return electrode for the second ablation power.

4. The apparatus according to claim 1, wherein the at least one electrode comprises a first electrode coupled to receive the first ablation power and a second electrode coupled to receive the second ablation power.

5. The apparatus according to claim 4, wherein the first electrode is configured as a source electrode for the first ablation power and as a return electrode for the second ablation power, and wherein the second electrode is configured as a source electrode for the second ablation power.

6. A method, comprising:
supplying first ablation power at a first frequency and second ablation power at a second frequency different from the first frequency, the first ablation power and the second ablation power being provided by a current source including a transformer with at least two selectable secondary taps;
receiving with at least one electrode the first and second ablation powers simultaneously;
measuring the first ablation power and the second ablation power, respectively, and selecting at least one of the taps so as to keep the first ablation power and the second ablation power, respectively, constant; and
dissipating the first and second ablation powers in body tissue in contact with the at least one electrode.

7. The method according to claim 6, wherein the at least one electrode consists of a single electrode.

8. The method according to claim 7, wherein the single electrode is configured as one of a first source electrode and a first return electrode for the first ablation power, and as one of a second source electrode and a second return electrode for the second ablation power.

9. The method according to claim 6, wherein the at least one electrode comprises a first electrode coupled to receive the first ablation power and a second electrode coupled to receive the second ablation power.

10. The method according to claim 9, wherein the first electrode is configured as a source electrode for the first ablation power and as a return electrode for the second ablation power, and wherein the second electrode is configured as a source electrode for the second ablation power.

* * * * *